US00PP37721P3

(12) United States Plant Patent
Bull

(10) Patent No.: US PP37,721 P3
(45) Date of Patent: Sep. 29, 2026

(54) ECHINACEA PLANT NAMED 'BULLECHIPUR 124'

(50) Latin Name: *Echinacea purpurea*
Varietal Denomination: BullEchipur 124

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,255

(22) Filed: Jun. 11, 2025

(65) Prior Publication Data

US 2026/0020510 P1 Jan. 15, 2026

Related U.S. Application Data

(60) Provisional application No. 63/731,837, filed on Jun. 12, 2024.

(51) Int. Cl.
*A01H 5/02* (2018.01)
*A01H 5/12* (2018.01)
*A01H 6/14* (2018.01)

(52) U.S. Cl.
USPC ..... Plt./428
CPC ..... *A01H 6/1448* (2018.05); *A01H 5/02* (2013.01); *A01H 5/12* (2013.01)

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS

| | | | |
|---|---|---|---|
| 7,982,110 | B2 | 7/2011 | Ren |
| PP31,064 | P2 | 11/2019 | Ren et al. |
| PP35,164 | P2 | 5/2023 | Rer |
| PP35,286 | P3 | 7/2023 | Bull |

OTHER PUBLICATIONS

Wist et al. Floral Structure and Dynamics of Nectar Production in *Echinacea pallida* var. *angustifolia* (*Asteraceae*), Int. J. Plant Sci. 169(6):708-722, 2008. (Year: 2008).*

Brookgreen Gardens *Echinacea purpurea* 'PAS702918', retrieved on Aug. 27, 2025 at https://www.brookgreen.ord/plantcollection/name/echinacea-purpurea-pas702918-powwow%25C2%25AE-white, 3 pages.

ThinkPlants Catalog, 2024-2025, retrieved on Sep. 4, 2025 at https://online.flippingbook.com/view/530070179/34/, 6 pages.

* cited by examiner

*Primary Examiner* — June Hwu
(74) *Attorney, Agent, or Firm* — The Webb Law Firm

(57) ABSTRACT

A new and distinct variety of *Echinacea* plant having a compact growth habit and numerous, pink colored blooms.

1 Drawing Sheet

Botanical classification: *Echinacea purpurea.*
Varietal denomination: 'BullEchipur 124'.

BACKGROUND OF THE INVENTION

The present invention comprises a new and distinct cultivar of *Echinacea* plant known by the varietal name 'BullEchipur 124'. The new variety was discovered in August of 2021 in Gönnebek, Germany as the result of a planned breeding program with the purposes of providing *Echinacea* plants with pink colored flowers, as well as a more compact growth habit, more uniformity, good branching, early flowering, clean green leaves, and good propagation when compared to prior *Echinacea* plants known to the breeder. The new variety is the result of a cross between an unpatented *Echinacea purpurea* variety having an internal breeder's reference of "BUL 2020-09" (female parent) and an unpatented *Echinacea purpurea* variety having an internal breeder's reference of "BUL 2020-22" (male parent) from the breeder's own collection. The new variety was first asexually reproduced via in-vitro tissue culture cuttings in Gönnebek, Germany in September of 2021. The new variety is similar to its parental varieties in botanical classification, but exhibits better branching, smaller green leaves, a different flower color, more compact growth habit, and earlier flowering than both of its parental varieties.

When 'BullEchipur 124' is compared to *Echinacea purpurea* variety named 'Pas702917' (unpatented), 'BullEchipur 124' is similar to 'Pas702917' in botanical classification and pink flower color, but the new variety exhibits earlier flowering, a more compact, even growth with increased branching, more flowers per plant, a shorter stature, and nice cleaner leaves that distinguish it from 'Pas702917'. Further, the following characteristics distinguish 'BullEchipur 124' when generally compared to other *Echinacea* varieties known to the breeder:

Compact growth habit;
Pink flower color;
High flower number per plant;
High branching;
A uniform growth habit;
Small, green leaves; and
A fast crop time.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWING

The accompanying photographic drawing illustrates the new variety at 21 weeks of age, with the color being as nearly true as is possible with color illustrations of this type.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 19 cm (3 liter) pots under normal field production conditions, and the color readings and measurements were observed outdoors under natural light on 21-week-old plants in Gönnebek, Germany. Color references are primarily to The 2015 R.H.S. Colour Chart of The Royal Horticultural Society of London, Sixth Edition, except where terms of ordinary significance are used.

PLANT

Time to initiate roots: About 7 days at approximately 19-20° C.

Time to develop roots: About 40-50 days at approximately 18° C.

Time to produce a finished flowering plant from a rooted cutting: About 12-14 weeks in a 19 cm container.

Rooting habit: Exhibits numerous roots that are freely branching and healthy in appearance.

Plant height: 40.0-45.0 cm.

Plant width: 30.0-35.0 cm.

Habit: Upright, medium compact growth with numerous branches.

Disease/pest resistance: Nothing unusual noted to date.

Temperature tolerance: Nothing unusual noted to date.

Drought tolerance: Average.

Branches (flowering stems):

*Number per plant.*—18-23.
*Length.*—2.0-35.0 cm.
*Diameter.*—3.0-8.0 mm.
*Internode length.*—1.0-6.0 cm.
*Angle.*—Upright and outward.
*Strength.*—Strong.
*Texture.*—Pubescence present.
*Color.*—Green (close to RHS 146B).

Foliage:

*Arrangement.*—Single, petiolate to sessile leaves.
*Leaf.*—Length: 3.0-18.0 cm. Width: 1.0-3.5 cm. Shape: Lanceolate. Apex: Acuminate. Base: Attenuate to acute. Margin: Entire. Rugosity: Medium to strong. Aspect: Straight to curved. Texture: Upper surface: Rough. Lower surface: Rough. Color: Young leaves: Upper surface: Green (close to RHS 137A). Lower surface: Green (close to RHS 137C). Mature leaves: Upper surface: Green (close to RHS 137A). Lower surface: Green (close to RHS 137C). Petiole: None present. Veins: Venation type: Cross-venulate to longitudinal. Color: Upper surface: Light green (close to 145A). Lower surface: Light green (close to 145B).

INFLORESCENCE

Bud:

*Diameter.*—1.0-3.5 cm.
*Length.*—1.2-2.5 cm.
*Color.*—Green (close to 137C) when closed and close to 187A when open.

Appearance: Elliptic-shaped ray florets and tubular-shaped disc florets.

Natural flowering season: Flowering occurs from July-September in Gönnebek, Germany, beginning approximately 10-11 weeks after planting.

Average number of inflorescences per plant: 18-25.

Average number of inflorescences per branch: 1-3.

Disc and ray floret arrangement: Single composite flower.

Fragrance: None.

Inflorescence:

*Diameter.*—3.0-7.0 cm.
*Height (depth).*—2.0-4.0 cm.
*Diameter of disc.*—1.5-4.0 cm.
*Height of disc.*—2.5-4.0 cm.
*Receptacle height.*—1.0 cm.
*Receptacle diameter.*—1.5-4.0 cm.

Ray florets:

*Number per inflorescence.*—15-22.
*Attitude.*—Horizontal; semi-drooping when mature.
*Profile.*—Weakly concave to flat.
*Arrangement.*—In two or three whorls.
*Length:* 1.5-3.5 cm.
*Width.*—0.8-1.2 cm.
*Shape.*—Elliptical.
*Apex.*—Obtuse to retuse with one or two notches (approximately 1-2 mm).
*Base.*—Acute.
*Margin.*—Entire.
*Texture.*—Upper surface: Smooth and glabrous. Lower surface: Rough.
*Color.*—When opening: Upper surface: Pink (close to NN74C). Lower surface: Pink (close to NN74D). At maturity: Upper surface: Pink (close to NN74C). Lower surface: Pink (close to NN74C). Ground color description: Pink.
*Venation.*—Appearance: Parallel. Color: Upper surface: Same color as the florets. Lower surface: Same color as the florets.

Disc florets:

*Number per inflorescence.*—Numerous; too many to quantify.
*Arrangement.*—In the center of receptacle.
*Length.*—8.0-15.0 mm.
*Width.*—1.0-2.0 mm.
*Shape.*—Tubular.
*Apex.*—Sharp.
*Color (receptacle spine with receptacle bracts).*—Immature: close to N186C. At maturity: close to 184A.
*Paleae.*—Color (Tip): Red-brown (close to N34A). Color (Below the tip): Red-orange (close to 34B).

Phyllaries:

*Number per inflorescence.*—35-50.
*Arrangement.*—In 3-4 whorls.
*Length.*—Approximately 0.5-1.0 cm.
*Width.*—2.0-3.0 mm.
*Shape.*—Lanceolate.
*Apex.*—Elongated oval.
*Base.*—Fused.
*Margin.*—Entire.
*Texture.*—Upper surface: Rough. Lower surface: Rough.
*Color.*—Immature: Upper surface: Green (close to NN137C). Lower surface: Green (close to NN137C).

At maturity: Upper surface: Green (close to NN137C). Lower surface: Green (close to NN137C).

Peduncles:

*Length* (*average*).—5.0-9.0 cm.

*Texture*.—Rough.

*Color*.—137B.

Reproductive organs:

Androecium:

*Presence*.—On disc florets.

*Number* (*per floret*).—One.

*Filament length*.—1.0-2.0 mm.

*Filament color*.—Brown-red (close to 184A).

*Anther*.—Shape: Oval. Length: 1.0 mm. Color: Brown-red (close to 184A).

*Pollen*.—Color: Yellow (close to 15B). Amount: Plentiful; too difficult to quantify.

Gynoecium:

*Presence*.—In disc and ray florets.

*Pistil length*.—1.0-2.0 mm.

*Stigma*.—Shape: Two-parted. Color: Brown-red (close to 184A).

*Style*.—Length: 1.0-2.0 mm. Color: Brown-red (close to 184A).

Seeds:

*Overall size*.—1.0-2.0 mm.

I claim:

1. A new and distinct variety of *Echinacea* plant named 'BullEchipur 124', as is herein illustrated and described.

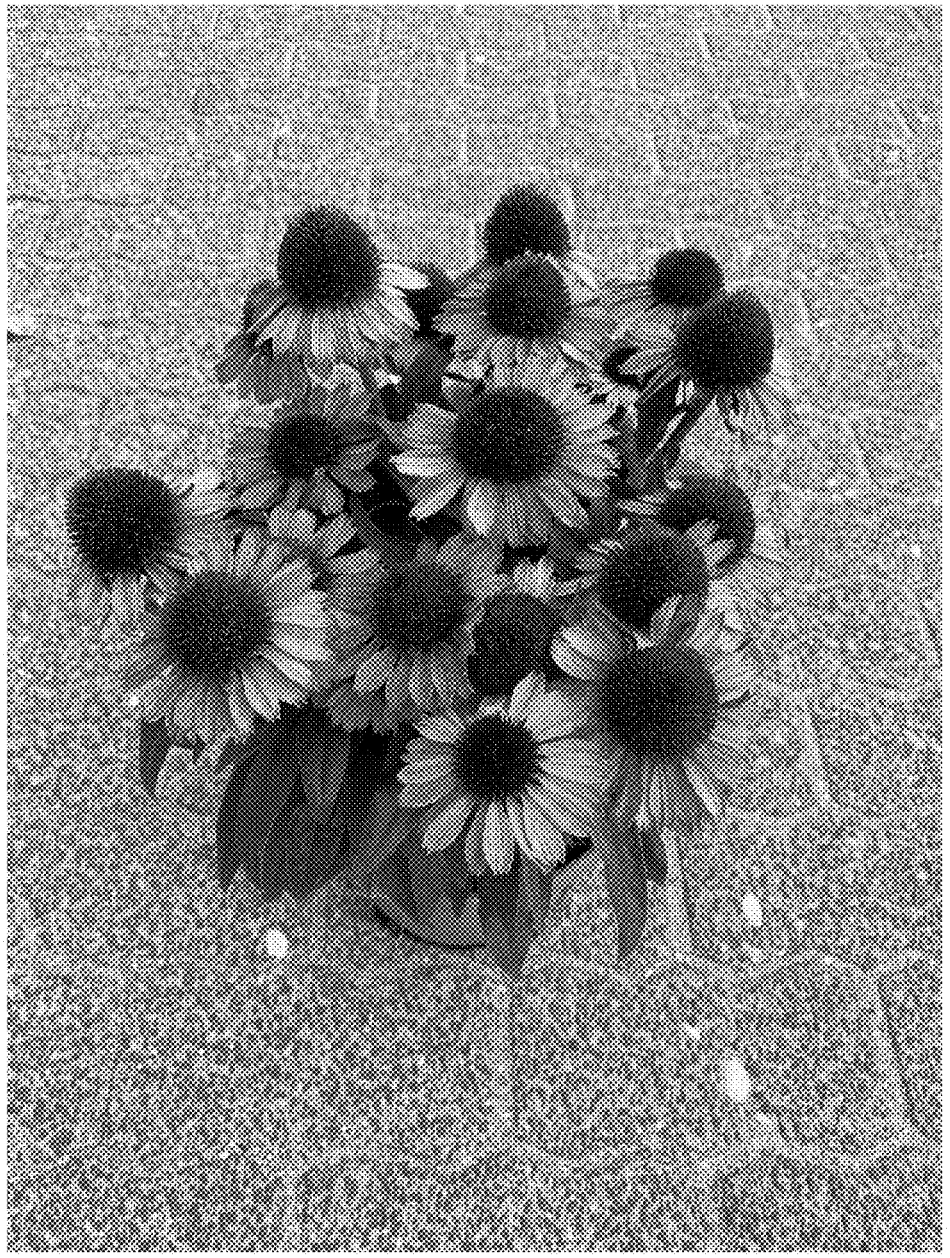

* * * * *